(12) United States Patent
Das et al.

(10) Patent No.: US 6,537,770 B1
(45) Date of Patent: Mar. 25, 2003

(54) ASSAY FOR DETECTING PHOSPHO-N-ACETYLMURAMYL-PENTAPEPTIDE TRANSLOCASE ACTIVITY

(75) Inventors: Kaveri Das, Bangalore (IN); Janakiraman Ramachandran, Bangalore (IN)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/582,466

(22) PCT Filed: Apr. 19, 2000

(86) PCT No.: PCT/SE00/00772

§ 371 (c)(1),
(2), (4) Date: Jun. 26, 2000

(87) PCT Pub. No.: WO00/65087

PCT Pub. Date: Nov. 2, 2000

(30) Foreign Application Priority Data

Apr. 22, 1999 (WO) .............................. PCT/IN99/00013

(51) Int. Cl.[7] .......................... C12Q 1/37; C12Q 1/48; C12Q 1/00; G01N 33/53
(52) U.S. Cl. .......................... 435/24; 435/23; 435/15; 435/4; 435/975
(58) Field of Search .......................... 435/24, 23, 15, 435/4, 975

(56) References Cited

FOREIGN PATENT DOCUMENTS

| EP | 0890644 | 1/1999 |
|----|---------|--------|
| EP | 0897007 | 2/1999 |
| WO | 9615258 | 5/1996 |
| WO | 0010587 | 3/2000 |
| WO | 200194622 A1 * | 6/2001 |

OTHER PUBLICATIONS

Cook, Neil D. *Scintillation proximity assay: a versatile high-throughput screening technology.* Drug Discovery Today 1: 287–294, 1996.

Brandish, P. E. et al. *Modes of Action of Tunicamycin, Liposidomycin B, and Mureidomycin A: Inhibition of Phospho-N-Acetylmuramyl-Pentapeptide Translocase from Escherichia Coli*, Antimicrobial Agents and Chemotherapy vol. 40, No. 7, pp. 1640–1644, 1996.

Brandish, P. E. et al. *Slow Binding Inhibition of Phospho-N-acetylmuramyl-pentapeptide-translocase (Escherichia Coli) by Mureidomycin A*, J. Biol. Chem. vol. 271, No. 13, pp. 7609–7614, 1996.

Weppner, W. A. et al. *Fluorescent Substrate of Nascent Peptidoglycan Synthesis URIDINE DIPHOSPHATE-N-ACETYLMURAMYL-N$^\epsilon$-5-DIMETHYLAMINONAPHTHALENE-1-SULFONYL)PENTAPEPTIDE* J. Biol. Chem. vol. 252, No. 7, pp. 2296–2303, 1977.

* cited by examiner

Primary Examiner—Louise N. Leary
(74) Attorney, Agent, or Firm—White & Case LLP

(57) ABSTRACT

The invention provides an assay for detecting phospho-N-acetylmuramyl-pentapeptide translocase enzyme activity, which comprises the steps of:

(1) incubating a reaction mixture comprising, in aqueous medium, N-succinimidyl [2,3-$^3$H] propionate substituted UDP-MurNAc-pentapeptide, N-succinimidyl propionate substituted UDP-MurNAc-pentapeptide (non-radioactive), a source of divalent metal ions, a source of undecaprenyl phosphate, a source of translocase enzyme and a detergent, under conditions suitable for enzyme activity to occur;

(2) acidification of the reaction mixture with a suitable buffer comprising a quaternary ammonium salt at pH~4.2 to stop the enzyme reaction of step (1); and (3) extraction of any undecaprenol-pyrophosphate-[2,3-$^3$H]propionate-N-acetylmuramylpentapeptide product formed and measuring radioactivity using a scintillation counter; and also a kit for use therein.

16 Claims, 1 Drawing Sheet

ASSAY FOR DETECTING PHOSPHO-N-ACETYLMURAMYL-PENTAPEPTIDE TRANSLOCASE ACTIVITY

The present invention relates to a new assay for the detection of phospho-N-acetylmuramyl-pentapeptide translocase enzyme activity (hereinafter referred to as "translocase enzyme").

Peptidoglycan is a major component of the bacterial cell wall that gives the wall its shape and strength. It is unique to bacteria and found in all bacteria, both gram-positive and gram-negative. Peptidoglycan is a polymer of glycan strands which are cross-linked through short peptide bridges. It consists of alternating β1–4 linked residues of N-acetyl glucosamine (GlcNAc) and N-acetyl muramic acid (MurNAc). A pentapeptide chain is attached to MurNAc (MurNAc-pentapeptide) and the peptidoglycan polymers are crosslinked through these peptide chains.

Biosynthesis of peptidoglycan can be divided into three stages: firstly, synthesis of the precursors in the cytoplasm, secondly, transfer of the precursors to a lipid carrier molecule and, thirdly, insertion of the precursors into the cell wall and coupling to existing peptidoglycan.

Enzymes responsible for the biosynthesis of the peptidoglycan component of the bacterial cell wall are novel targets for the design of new antibiotics. Owing to the worldwide emergence of bacterial strains resistant to current antibiotics, it has become necessary to develop new antimicrobial agents. The translocase enzyme catalyses the first step in the membrane cycle of peptidoglycan biosynthesis, namely the transfer of phospho-N-acetylmuramyl-L-Ala-γ-D-Glu-m-diaminopimellic acid-D-Ala-D-Ala from Uridine 5'-diphosphate phospho-N-acetylmuramyl-L-Ala-γ-D-Glu-m-diaminopimellic acid-D-Ala-D-Ala (hereinafter referred to as "UDP-MurNAc-pentapeptide" or "UDP-MPP") to a membrane-bound lipid carrier, undecaprenyl phosphate. The translocase enzyme is encoded by the mraY gene in *Escherichia coli*. the translocase enzyme is essential for bacterial viability (see D. Mengin-Lecreulx, L. Texier, M. Rousseaue and J. Van Heijernoot, J. Bacteriol., (1991), 173, 4625–4636).

No commercial antibiotics in current use are directed against the translocase enzyme. It therefore represents a target for novel antibacterial agents which has as yet been unexploited.

The translocase enzyme is usually assayed by radiolabelling the UDP-MurNAc-pentapeptide and monitoring the transfer of phospho-N-acetylmuramyl pentapeptide from the UDP-MurNAc-pentapeptide to undecaprenyl phosphate, resulting in the formation of a lipid intermediate, Lipid I. The radiolabelling is usually done either by using the enzyme Ligase to label the D-Alanine-D-Alanine end or by the in vivo incorporation on the membrane. Both these methods produce low yields and thus are not cost effective in developing high-throughput-screening (HTS) assays.

The translocase enzyme activity may alternatively be assayed using a fluorescent substrate such as dansyl chloride as described by Brandish et al., J. Biol. Chem., (1996), 271, 7609–7614. However, certain compounds may quench the fluorescence, thus resulting in picking up false inhibitors of the enzyme reaction.

It would be desirable to develop an assay for the translocase enzyme that is suitable for high-throughput screening.

In accordance with the present invention, there is therefore provided an assay for detecting phospho-N-acetylmuramyl-pentapeptide translocase enzyme activity, which comprises the steps of:

(1) incubating a reaction mixture comprising, in aqueous medium, N-succinimidyl [2,3-$^3$H] propionate substituted UDP-MurNAc-pentapeptide, N-succinimidyl propionate substituted UDP-MurNAc-pentapeptide (non-radioactive), a source of divalent metal ions, a source of undecaprenyl phosphate, a source of translocase enzyme and a detergent, under conditions suitable for enzyme activity to occur;

(2) acidification of the reaction mixture with a suitable buffer comprising a quaternary ammonium salt at pH~4.2 to stop the enzyme reaction of step (1); and (3) extraction of any undecaprenol-pyrophosphate-[2,3-$^3$H]propionate-N-acetylmuramylpentapeptide product formed and measuring radioactivity using a scintillation counter.

In step (1), the UDP-MPP used may be any of those normally present in naturally occurring peptidoglycans. It is conveniently purified from bacteria or made enzymatically with precursors from bacteria, for example by methods similar to that described by Blaauwen et al.; J. Bacteriol. (1990), 172, 63–70. Alternatively, it may be isolated from cells of *B.subtilits* W23 by the methodology described by Lugtenberg et al.; J. Bacteriol. (1972), 109, 326–335. The preferred UDP-MPP to use is UDP-MurNAc-L-Alanine-γ-D-glutamic acid-m-diaminopimellic acid-D-alanine-D-alanine from *Bacillus cereus*.

The UDP-MPP thus obtained is reacted with N-succinimidyl [2,3-$^3$H]propionate (commercially available from Amersham Ltd.) to obtain N-succinimidyl [2,3-$^3$H] propionate substituted UDP-MurNAc-pentapeptide (hereinafter referred to as "$^3$H-propionated UDP-MPP").

The concentration of $^3$H-propionated UDP-MPP used in the assay will typically be in the range from 2 to 50 μM, preferably from 2 to 40 μM and more preferably from 2 to 25 μM.

The concentration of the unlabelled, non-radioactive N-succinimidyl propionate substituted UDP-MPP (hereinafter referred to as "propionated non-radioactive UDP-MPP") also used in the reaction may be in the range from 5 to 70 μM, preferably from 5 to 50 μM and especially from 8 to 30 μM.

Divalent metal ions used in the reaction are preferably magnesium ions. A suitable source of magnesium ions is magnesium chloride. The concentration of divalent metal ions used may be in the range from 20 mM to 100 mM, preferably from 20 mM to 80 mM, more preferably from 20 mM to 50 mM, e.g. 25 mM.

In addition, potassium chloride at a concentration in the range from 50 mM to 100 mM may be added to the reaction mixture.

The membranes of *Escherichia coli* bacteria may conveniently be used and indeed are preferred as a source of undecaprenyl phosphate and translocase enzyme. The quantity of membranes used will typically be in the range from 5 to 200 μg, preferably 50 μg, per 50 μl of the reaction mixture. The membranes may be prepared by methods known in the art.

The aqueous medium used in step (1) is preferably a buffer solution, e.g. of Tris [hydroxymethyl] aminomethane hydrochloride ("Tris-HCl"), having a pH of about 7.5. Tris-HCl is commercially available from the Sigma Aldrich Co. Ltd.

The reaction mixture may additionally contain 0.01 unit of alkaline phosphatase.

The detergent used may, for example, be Triton X-100 in a concentration of 0.1% w/v. The detergent may be effective in solubilising the bacterial membranes if these are used.

If the assay is intended to be used as a screen for identifying anti-bacterial compounds that are antagonists of the translocase enzyme, the reaction mixture in step (1) may further comprise one or more test compounds in varying concentrations. Since translocase is the enzyme required in the first step of peptidoglycan synthesis, it represents a suitable target for the development anti-bacterial drugs.

The reaction mixture of step (1) is maintained at a temperature in the range from 20° C. to 37° C., preferably 25° C., for a short period of time, e.g. up to 10 minutes, specifically 6–8 minutes.

The enzyme reaction is stopped by the addition of, for example, 6M pyridinium acetate and n-butanol (pH~4.2) in a 2:1 mixture. This constitutes step (2).

In step (3), the product is extracted using, for example, n-butanol. It is then quantified in a scintillation counter.

The present invention will be further illustrated with reference to the following Example.

EXAMPLE 1

Eppendorf tubes were individually filled with a total of 40 $\mu$l of the reaction mixture each, initially. The reaction mixture consisted of an aqueous buffer solution of 100 mM Tris-HCl (Tris[hydroxymethyl]aminomethane hydrochloride), 25 mM magnesium chloride, 50 Mm of potassium chloride, 0.1% w/v Triton X-100, 8 $\mu$M of propionated non-radioactive UDP-MPP, 2 $\mu$M of $^3$H-propionated UDP-MPP at room temperature, 10 $\mu$l of the enzyme at a concentration of 5 $\mu$g per ml and 17.5 $\mu$l of water. To this a solution of a test compound (e.g. Tunicamycin) of varying concentration is added. Tunicamycin is a known antagonist of the translocase enzyme. The reaction commences with the addition of the enzyme.

The *Escherichia coli* membranes, which serve as a source of the enzyme, were prepared in the following manner.

The membranes are prepared from spheroplast pellets which are commercially available. Each pellet contains a certain amount of *E. coli* Hfr H. The pellet is thawed overnight at 4° C. The pellet is weighed and the figure is multiplied by 7.5. This gives the volume of the buffer solution to be added to it. The buffer solution used is 20 $\mu$M Tris-HCl of pH 8.0, containing 20% sucrose. The mixture is stirred gently for 10 minutes using a magnetic stirrer in cold. To this is added, a solution of egg white lysozyme, till the concentration to get a final concentration of 0.2 mg per ml. It is stirred on ice for another 10 minutes. To this, EthyleneDiamineTetraacetic Acid (EDTA), commercially available from Sigma Aldrich Co. Ltd., of concentration 0.2 M in 20 Mm Tris-HCl of pH 8.0, is added slowly over a period of one hour until a final concentration of 0.02M is obtained. This addition is carried out in a cold room at a temperature of 4–8° C. The mixture is then centrifuged at 12,000 g for 20 minutes. The pellet is again resuspended in the same volume of 50 mM Tris-HCl buffer solution of pH 7.5 as calculated in the previous paragraph, containing, 20 $\mu$g/ml DNAse, 20 $\mu$g/ml RNAse, 1 mM magnesium chloride and 1 mM $\beta$-mercapto ethanol. This is stirred at room temperature for one hour until the sample becomes homogeneous. The membrane fraction is recovered by spinning in an ultra-centrifuge at 1,000,000 g for an hour.

The $^3$H-propionated UDP-MPP used as the substrate is prepared in the following manner.

A fixed volume of 4 O.D. at a wavelength of 262 nm i.e. approximately 450–500 $\mu$g unlabeled UDP-MPP is taken in an empty eppendorf tube. In another eppendorf tube, 0.5 mCi of tritiated N-succinimidyl propionate (N-succinimidyl [2,3-$^3$H]propionate) is taken and to this, about 180 $\mu$l of 1% NaHCO$_3$ is added. The second tube is mixed well and transferred to the first tube. The second tube is rinsed well, with 180 $\mu$l of 1% NaHCO$_3$ and again transferred to the first tube. The tube, containing the mixture, is left overnight on a shaker at room temperature to facilitate labelling. In a similar manner, propionated non-radioactive UDP-MPP is prepared, using N-succinimidyl propionate instead of the radioactive compound.

It is purified as follows, (1) A glass column is packed with 1 ml of sephadex A-25, commercially available.

(2) The column is washed with a 10 bed volume of water.

(3) It is then equilibrated with a 10 bed volume of 1% NaHCO$_3$.

(4) The reaction mixture is loaded onto the column and the flow through is collected.

(5) The flow through is passed through the column twice, to facilitate binding.

(6) The column is then washed with 0.5 ml of 1% NaHCO$_3$.

(7) The wash and flow through is collected in the same tube and labelled.

(8) The column is washed with 6 ml of 1% NaHCO$_3$, twice.

(9) The two washings are collected in the same tube and labelled.

(10) The column is eluted with 1 ml of 1% NaHCO$_3$, containing 0.4M lithium chloride.

(11) The fractions are collected and labelled.

(12) The fractions are counted, and the purest ones used in the reaction.

The eppendorf tube containing the reaction mixture is incubated at 37° C. for about 4 to 60 minutes and thereafter, every two minutes, 50 $\mu$l of a 2:1 mixture of pyridinium acetate and n-butanol is added to stop the reaction.

The product is extracted with saturated n-butanol and washed with 50 $\mu$l of water. It is then counted, 25–50 $\mu$l at a time on a scintillation counter.

The reaction catalysed by the enzyme translocase is known to be reversible. To show the reversible reaction, the enzyme reaction was continued for 10 mintues to form the radioactive product, undecaprenol-pyrophosphate-[2,3-$^3$H] propionate-N-acetylmuramylpentapeptide, Lipid I. This is seperated from its organic phase. Once the radioactive product is formed one set of reactions is stopped using the 2:1 pyridinium acetate and n-butanol mixture as described before. In a parallel set of reactions, 1 $\mu$M UMP is added. The reaction is then stopped after about 3–4 minutes. The lipid fraction can be extracted from both the sets of reactions. It is seen that radioactive count in the organic phase is reduced to basal levels with UMP. This indicates the reversal of Lipid I to the water soluble precursor.

This example goes to show that the present assay system is specific for only the translocase reaction, even when a particulate membrane was used as the enzyme source.

Figure 1:
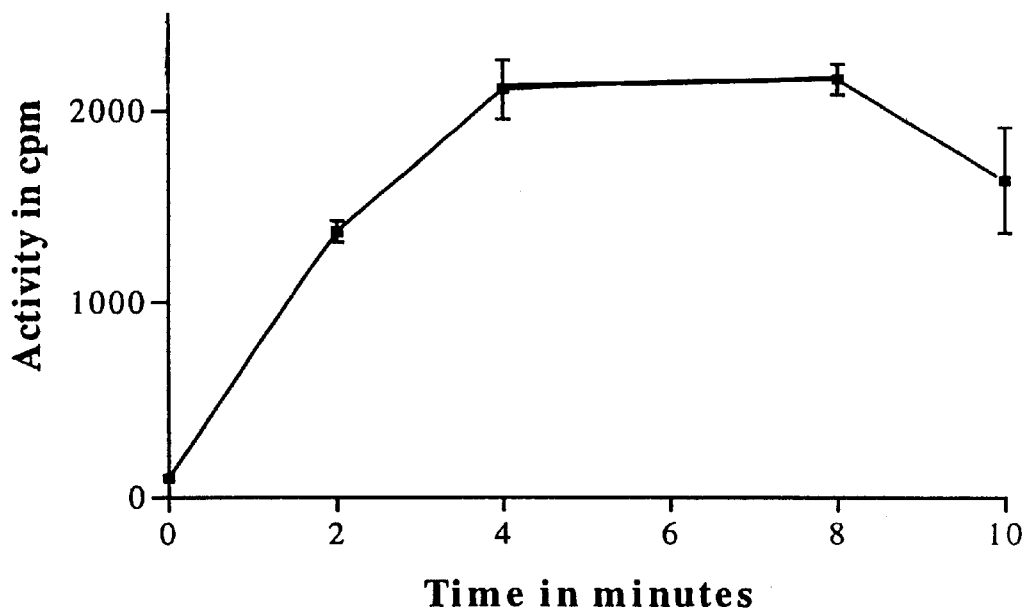
FIG. 1 is a graph showing the counts per minute (cpm) versus time based on the readings taken from the 100% controls.
Figure 2:
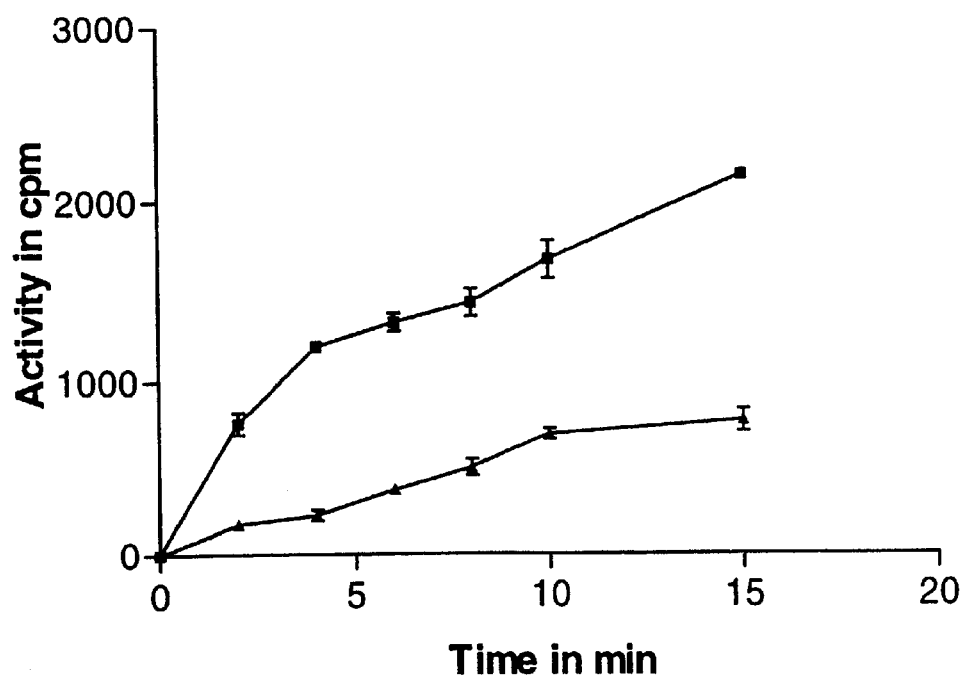
FIG. 2 shows the rate of inhibition of translocase by Tunicamycin at 0.3 $\mu$g/ml concentration (indicated by ▲) compared with the control (indicated by ■). This confirms that Tunicamycin is an antagonist of the translocase enzyme.

We claim:

1. An assay for detecting phospho-N-acetylmuranyl-pentapeptide translocase enzyme activity, which comprises the steps of:
    (1) incubating a reaction mixture comprising, in aqueous medium, N-succinimidyl [2,3-$^3$H] propionate substituted UDP-MurNAc-pentapeptide, N-succinimidyl propionate substituted non-radioactive UDP-MurNAc-pentapeptide, a source of divalent metal ions, a source of undecaprenyl phosphate, a source of translocase enzyme and a detergent, under conditions suitable for enzyme activity to occur;
    (2) acidifying the reaction mixture with a buffer comprising a quaternary ammonium salt at pH-4.2 to stop the enzyme reaction of step (1); and
    (3) extracting any undecaprenol-pyrophosphate-[2,3-$^3$H] propionate-N-acetylmuramylpentapeptide product formed and measuring radioactivity using a scintillation counter.

2. The assay according to claim 1, wherein the UDP-N-acetylmuramylpentapeptide is UDP-MurNAc-L-Alanine-γ-D-glutamic acid-m-diaminopimellic acid-D-alanine-D-alanine.

3. The assay according to claim 1 or claim 2, wherein the source of divalent metal ions is magnesium chloride.

4. The assay according to claim 1, wherein the source of one or both of undecaprenyl phosphate and translocase enzyme is bacterial cell membranes.

5. The assay according to claim 4, wherein the bacterial cell membranes are from *Escherichia coli*.

6. The assay according to claim 1, wherein the reaction mixture of step (1) further comprises a test compound.

7. The assay according to claim 6, wherein the test compound is an antagonist of the translocase enzyme.

8. The assay according to claim 1, wherein a 2:1 mixture of pyridinium acetate and n-butanol is used to stop the reaction in step (2).

9. The assay according to claim 1, wherein the product in step (3) is extracted using n-butanol.

10. A kit for performing an assay according to claim 1, which comprises,
    (1) N-succinimidyl [2,3-$^3$H] propionate substituted UDP-MurNAc-pentapeptide,
    (2) N-succinimidyl propionate substituted non-radioactive UDP-MurNAc-pentapeptide,
    (3) a source of divalent metal ions,
    (4) a source of undecaprenyl phosphate,
    (5) a source of phospho-N-acetylmuramyl-pentapeptide translocase enzyme, and
    (6) a detergent.

11. The kit according to claim 10, wherein the UDP-N-acetylmuramylpentapeptide is UDP-MurNAc-L-Alanine-γ-D-glutamic acid-m-diaminopimellic acid-D-alanine-D-alanine.

12. The kit according to claim 10, wherein the source of divalent metal ions is magnesium chloride.

13. The kit according to claim 10, wherein the source of one or both of undecaprenyl phosphate and translocase enzyme is bacterial cell membranes.

14. The kit according to claim 13, wherein the bacterial cell membranes are from *Escherichia coli*.

15. The kit according to claim 10, wherein the assay comprises a reaction mixture comprising a test compound.

16. The kit according to claim 10, wherein the test compound is an antagonist of the translocase enzyme.

* * * * *